(12) United States Patent
Hoashi et al.

(10) Patent No.: US 10,195,154 B2
(45) Date of Patent: Feb. 5, 2019

(54) METHOD FOR PRODUCING ORODISPERSIBLE TABLETS

(75) Inventors: Yohei Hoashi, Osaka (JP); Naohisa Katayama, Osaka (JP); Shunsuke Daidouji, Osaka (JP)

(73) Assignee: Nipro Corporation, Osaka-shi (JP)

( * ) Notice: Subject to any disclaimer, the term of this patent is extended or adjusted under 35 U.S.C. 154(b) by 960 days.

(21) Appl. No.: 14/125,240

(22) PCT Filed: Jun. 8, 2012

(86) PCT No.: PCT/JP2012/064788
§ 371 (c)(1),
(2), (4) Date: Dec. 10, 2013

(87) PCT Pub. No.: WO2012/169614
PCT Pub. Date: Dec. 13, 2012

(65) Prior Publication Data
US 2014/0093567 A1  Apr. 3, 2014

(30) Foreign Application Priority Data

Jun. 10, 2011 (JP) .................. 2011-129812

(51) Int. Cl.
| A61K 9/28 | (2006.01) |
| A61K 9/00 | (2006.01) |
| A61K 9/20 | (2006.01) |
| A61K 9/50 | (2006.01) |
| A61K 31/00 | (2006.01) |
| A61K 31/196 | (2006.01) |
| A61K 31/4178 | (2006.01) |

(52) U.S. Cl.
CPC .......... *A61K 9/2893* (2013.01); *A61K 9/0056* (2013.01); *A61K 9/2004* (2013.01); *A61K 9/2018* (2013.01); *A61K 9/2081* (2013.01); *A61K 9/5026* (2013.01); *A61K 31/00* (2013.01); *A61K 31/196* (2013.01); *A61K 31/4178* (2013.01)

(58) Field of Classification Search
CPC .. A61K 9/2893; A61K 9/0056; A61K 9/2004; A61K 9/2018; A61K 9/2081; A61K 9/5026; A61K 31/00; A61K 31/196; A61K 31/4178
USPC .......................................................... 424/474
See application file for complete search history.

(56) References Cited

U.S. PATENT DOCUMENTS

| 4,968,505 A | 11/1990 | Okada et al. | |
| 5,409,711 A | 4/1995 | Mapelli et al. | |
| 6,451,345 B1 | 9/2002 | Percel et al. | |
| 7,431,942 B2 * | 10/2008 | Shimizu ............... | A61K 9/0056 424/464 |
| 2004/0220276 A1 | 11/2004 | Cousin et al. | |
| 2008/0248111 A1 * | 10/2008 | Chaudhari ........... | A61K 9/0056 424/465 |

FOREIGN PATENT DOCUMENTS

| CA | 2298487 A1 | 2/1999 |
| EP | 1980244 A2 | 10/2008 |
| EP | 1980244 A3 | 11/2010 |
| EP | 2258350 A2 | 12/2010 |
| EP | 2258350 A3 | 8/2012 |
| JP | 2237918 A | 9/1990 |
| JP | 5500674 A | 2/1993 |
| JP | 8208517 A | 8/1996 |
| JP | 10101582 A | 4/1998 |
| JP | 2001106639 A | 4/2001 |
| JP | 2001302510 A | 10/2001 |

\* cited by examiner

*Primary Examiner* — Adam C Milligan
(74) *Attorney, Agent, or Firm* — The Webb Law Firm

(57) ABSTRACT

A method for easily producing orodispersible tablets that secure an eluting behavior of a principal agent in the digestive tract and mask unpleasant taste in the oral cavity is provided. Provided is a method for producing orodispersible tablets which includes mixing an additive to a principal agent to form principal agent particles as a granulation process, coating the principal agent particles with a coating agent to form coated particles as a coating process, and tableting the coated particles to form tablets as a tableting process, wherein the additive used in the granulation process contains a pH regulator, and the coating agent used in the coating process contains a pH-dependent polymer dissolving at pH 5 or more.

4 Claims, 1 Drawing Sheet

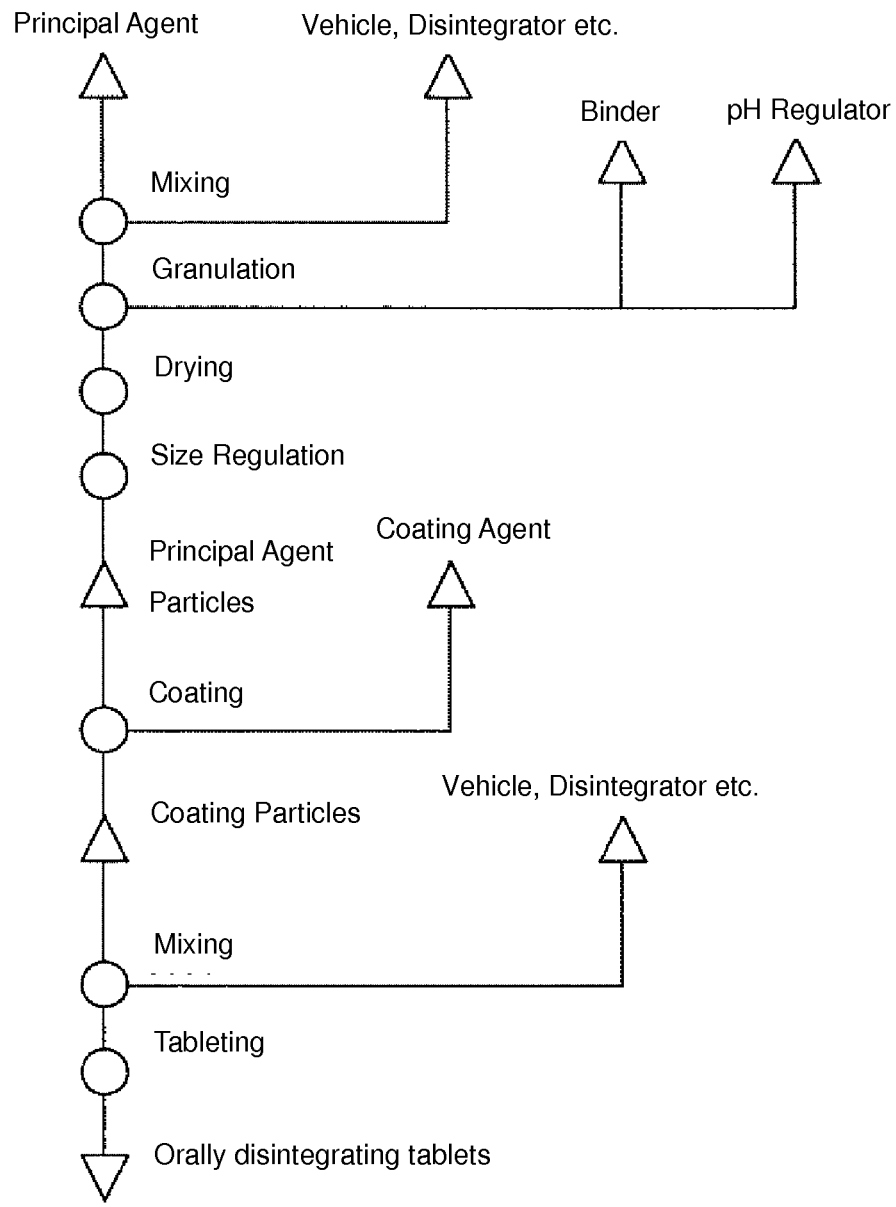

METHOD FOR PRODUCING ORODISPERSIBLE TABLETS

CROSS-REFERENCE TO RELATED APPLICATIONS

This application is the United States national phase of International Application No. PCT/JP2012/064788 filed Jun. 8, 2012, and claims priority to Japanese Patent Application No. 2011-129812 filed Jun. 10, 2011, the disclosures of which are hereby incorporated in their entirety by reference.

TECHNICAL FIELD

The present invention relates to a method for producing orodispersible tablets.

BACKGROUND ART

Since an orally disintegrating tablet is a dosage form that enables elderly people, children, and patients who have difficulty in swallowing to easily take the medicine and can be taken without water, it has attracted attention as a dosage form that improves a patient's quality of life (QOL).

Although orodispersible tablets disintegrate in the oral cavity within 30 seconds after being taken, and can be taken without water, some of them have an unpleasant taste such as a bitter taste (astringent taste) caused by the principal agent in the oral cavity.

Therefore, methods for masking an unpleasant taste caused by the principal agent have been developed. Although the easiest method is a method for concealing an unpleasant taste by adding a sweetening agent such as aspartame, stevia, and sugar alcohol, and a flavor such as L-menthol (e.g., see Patent Documents 1 to 4), it is hard to mask an unpleasant taste by these methods.

PRIOR ART DOCUMENTS

Patent Documents

Patent Document 1: Japanese Laid-Open Patent Publication No. H8-208517
Patent Document 2: Japanese Laid-Open Patent Publication No. H10-101582
Patent Document 3: Japanese Laid-Open Patent Publication No. 2001-302510
Patent Document 4: Japanese Laid-Open Patent Publication No. 2001-106639

SUMMARY OF INVENTION

Problems to be Solved by the Invention

It is an object of the present invention to provide a method for easily producing orodispersible tablets that secure elution of a principal agent in the digestive tract and mask an unpleasant taste in the oral cavity.

Means for Solving the Problems

As a result of intensive examination to solve the problems described above, the present inventors found that it was possible to easily produce orodispersible tablets that secure elution of a principal agent in the digestive tract and mask an unpleasant taste in the oral cavity by adding a pH regulator in a granulation process in which the principal agent particles are formed, and adding a pH-dependent polymer dissolving at pH 5 or more in a coating process in which coated particles are formed from the principal agent particles, and the present invention was achieved.

The present invention provides a method for producing orodispersible tablets which comprises:
mixing an additive to a principal agent to form principal agent particles as a granulation process;
coating the principal agent particles with a coating agent to form coated particles as a coating process; and
tableting the coated particles to form tablets as a tableting process;
wherein the additive used in the granulation process contains a pH regulator, and
the coating agent used in the coating process contains a pH-dependent polymer dissolving at pH 5 or more.

In one embodiment, the principal agent is an acidic substance.

In one embodiment, the pH regulator is an acidic substance.

The present also provides an orally disintegrating tablet produced by the above producing method.

Effects of Invention

The present invention can provide a method for easily producing orodispersible tablets that secure elution of a principal agent in the digestive tract and mask an unpleasant taste in the oral cavity.

BRIEF DESCRIPTION OF DRAWINGS

The drawing is a flow chart showing a method for producing orodispersible tablets of the present invention.

DESCRIPTION OF THE INVENTION

In the present invention, a principal agent refers to an effective ingredient, and a tablet refers to a solid dosage form of pharmaceutical preparation obtained by shaping the principal agent to which additives such as a vehicle, a binder, and a disintegrator are added into a fixed form by a method such as compression forming. An orally disintegrating tablet refers to a tablet prepared so as to disintegrate in the oral cavity without water when being taken.

A method for producing orodispersible tablets of the present invention includes to form principal agent particles from to a principal agent as a granulation process, coating the principal agent particles with a coating agent to form coated particles as a coating process and tableting the coated particles to form tablets as a tableting process. The outline of the flow chart is shown in FIG. 1.

(Granulation Process)

In the production method of the present invention, first, principal agent particles are formed (granulated) from the principal agent in the granulation process. The principal agent particles contain additives such as a vehicle, a disintegrator, a fluidizer, a pH regulator, and a binder in addition to the principal agent.

Granulation is performed by mixing additives into the principal agent. The principal agent and the additives may be crushed as appropriate to be used. A mixing amount and a mixing method are selected as appropriate. There is no particular limitation on the mixing method, and examples thereof include a method in which powders of the principal agent and the additives are mixed, and a method in which solutions obtained by dissolving the principal agent and the additives in solvents such as water are mixed, and then the solvent is evaporated. The granulation method may be either a wet granulation method or a dry granulation method. There is no particular limitation on the wet granulation method, and examples thereof include a method using a fluidized bed granulating dryer, a mixer granulator, a cylindrical extrusion granulator, a rolling fluidized bed granulating coating apparatus, a spray drier, or the like. There is no particular limitation on the dry granulation method, and examples thereof include a method using a roller compactor or the like. There is no limitation on the form of the principal agent particle obtained by the granulation, and examples thereof include a fine grain and a granule. There is no limitation on the size of the principal agent particle. For example, the size of the principal agent particle is 10 to 500 µm, and preferably 50 to 200 µm. A particle size regulation may be performed on the principal agent particles as appropriate. There is no particular limitation on a method of the particle size regulation, and examples thereof include a method using a sizing apparatus or a classifying apparatus.

The principal agent in the present invention is not particularly limited, but is preferably an acidic substance. The acidic substance is a substance that releases a hydrogen ion ($H^+$) in an aqueous solution. The acidic substance often exists as an ion (dissociated type) in an aqueous solution of pH higher than the pKa (acid dissociation constant) of the substance, and conversely, the acidic substance often exists as a molecule (non-dissociated type) in an aqueous solution of pH lower than the pKa. There is no particular limitation on the acidic substances, and examples thereof include substances having an aromatic hydroxyl group (—OH), a carboxyl group (—COOH), a phosphate group (—$PO_3H$), a sulfo group (—$SO_3H$), and the like. Specific names thereof are as follows: aspirin, ibuprofen, naproxen, diclofenac sodium, indomethacin, ketoprofen, meloxicam, dihydrocodein phosphate, ephedrine hydrochloride, chlorpheniramine maleate, cephalexin, warfarin, furosemide, clofibrate, captopril, salicylic acid, digitoxin, diflunisal, sulindac, cefazolin, cefamandole, cefoxitin, thiopental, tolmetin, valproic acid, phenytoin, bumetanide, benzylpenicillin, pentobarbital, methotrexate, metolazone, tetracycline, piroxicam, etodolac, caffeine, theophylline, ursodeoxycholic acid, glibenclamide, glimepiride, and losartan potassium. There is no particular limitation on the drug effect of the principal agent. The principal agent may be a substance having bitter taste. There is no particular limitation on the form of the principal agent, and examples thereof include a powder-like form, a solid form, and a granular form.

There is no particular limitation on vehicles, and examples thereof include cellulose (e.g., crystalline cellulose, ethyl cellulose, hydroxypropyl cellulose having a low degree of substitution, and hydroxypropyl methyl cellulose (hypromellose)) and derivatives thereof, starch (e.g., corn starch, potato starch, wheat starch, rice starch, partially pregelatinized starch, and hydroxypropyl starch) and derivatives thereof, sugar (e.g., glucose, lactose, white sugar (including sucrose), powdered sugar, trehalose, dextran, and dextrin), sugar alcohol (e.g., mannitol, xylitol, sorbitol, and erythritol), glycerin fatty acid ester, inorganic powder (e.g., magnesium aluminometasilicate and synthetic hydrotalcite), and inorganic salt such as light anhydrous silicic acid, anhydrous calcium phosphate, precipitated calcium carbonate, calcium silicate, calcium hydrogenphosphate hydrate, and sodium bicarbonate. The vehicle is preferably mannitol, lactose, crystalline cellulose or starch. These substances can be used alone or in a combination of two or more.

There is no particular limitation on disintegrators, and examples thereof include substances used in the tableting process described below. The disintegrator is preferably croscarmellose sodium, sodium starch glycolate, or crospovidone. These substances can be used alone or in a combination of two or more.

There is no particular limitation on fluidizers, and examples thereof include hydrous silicon dioxide, light anhydrous silicic acid, talc, synthetic aluminum silicate, titanium oxide, stearic acid, magnesium stearate, calcium stearate, and magnesium aluminometasilicate. The fluidizer is preferably hydrous silicon dioxide, light anhydrous silicic acid, or talc. These substances can be used alone or in a combination of two or more.

A pH regulator is preferably an acidic substance. As described above, the acidic substance is a substance that releases a hydrogen ion ($H^+$) in an aqueous solution. The acidic substance often exists as an ion (dissociated type) in an aqueous solution of pH higher than the pKa (acid dissociation constant) of the substance, and conversely, the acidic substance often exists as a molecule (non-dissociated type) in an aqueous solution of pH lower than the pKa. There is no particular limitation on acidic substances used as the pH regulator, and examples thereof include organic acid that is solid at ordinary temperature such as adipic acid, citric acid, malic acid, fumaric acid, succinic acid, tartaric acid, aspartic acid, and glutamic acid, or salts thereof. The pH regulator is preferably citric acid, malic acid, or succinic acid. These substances can be used alone or in a combination of two or more. A prescribed dose of the pH regulator per 1 g of the principal agent is normally 10 to 1,000 mg, preferably 20 to 500 mg, and more preferably 50 to 200 mg. If it is greater than 1,000 mg, elution of the principal agent in the digestive tract is delayed, and the expected drug effect is not obtained. If it is less than 10 mg, the principal agent elutes in the oral cavity, and therefore the expected masking effect is not obtained.

There is no particular limitation on binders, and examples thereof include methyl cellulose, hydroxyethyl cellulose, hydroxypropyl cellulose, hypromellose, gelatin, agar, alginic acid, sodium alginate, dextrin, xanthan gam, powdered acacia, polyvinyl pyrrolidone, partially saponified polyvinyl alcohol, pullulan, and partially pregelatinized starch. The binder is preferably hydroxypropyl cellulose, hypromellose, or polyvinyl pyrrolidone. These substances can be used alone or in a combination of two or more.

(Coating Process)

Then, in the method for producing of the present invention, the principal agent particles are coated with a coating agent to form coated particles in the coating process.

There is no particular limitation on the coating method, and examples thereof include a spray coating in which a coating solution is prepared by dissolving or dispersing a coating agent in a solvent such as water and sprayed on the principal agent particles. In addition, examples thereof include a pan coating, a flow coating, and a roll coating. There is no particular limitation on the form of the coated particles obtained by coating the principal agent particles. There is no particular limitation on the size of the coated particles. For example, the particle size is 10 to 1,000 µm, and preferably 50 to 500 µm.

The coating agent contains a pH-dependent polymer dissolving at pH 5 or more. There is no particular limitation on the pH-dependent polymers dissolving at pH 5 or more, and examples thereof include methacrylic acid copolymer L (common name; product name; EUDRAGIT L), methacrylic acid copolymer LD (common name; product name;

EUDRAGIT L30-D55), methacrylic acid copolymer S (common name; product name; EUDRAGIT S), hypromellose phthalic ester, hydroxypropyl methyl cellulose acetate succinate, carboxymethyl ethyl cellulose, and shellac. The coating agent is preferably methacrylic acid copolymer LD. These substances can be used alone or in a combination of two or more. A prescribed dose of the pH-dependent polymer dissolving at pH 5 or more per 1 g of the principal agent is normally 50 to 2,000 mg, preferably 100 to 1,000 mg, and more preferably 200 to 500 mg. If it is greater than 2,000 mg, elution of the principal agent in the digestive tract is delayed, and the expected drug effect is not obtained. If it is less than 50 mg, the principal agent elutes in the oral cavity, and therefore the expected masking effect is not obtained.

The coating agent may contain other bases. There is no particular limitation on other bases, and examples thereof include sugar, sugar alcohol, methyl cellulose, ethyl cellulose, hydroxypropyl cellulose, hypromellose, triethyl citrate, triacetin, polyethylene glycol (PEG) such as macrogol, polysorbate, talc, and titanium oxide. The other base is preferably sugar, sugar alcohol, triacetin, PEG such as macrogol, or talc. There is no particular limitation on the sugars, and examples thereof include glucose, fructose, lactose, white sugar, reduced maltose, and trehalose. There is no particular limitation on the sugar alcohols, and examples thereof include mannitol, erythritol, sorbitol, xylitol, maltitol, and lactitol. The sugar alcohol is preferably mannitol. These substances can be used alone or in a combination of two or more.

The production method of the present invention may include an over-coating process following the coating process. The over-coating method and the coating agent correspond to the coating process described above.

(Tableting Process)

Then, in the production method of the present invention, the coated particles are tableted to form tablets in the tableting process.

The coated particles mixed with a vehicle, a binder, a disintegrator, a corrigent, and a lubricant are tableted. There is no particular limitation on the tableting method, and examples thereof include a method performed with a hydraulic hand press, a single punch tableting apparatus, a rotary tableting apparatus, and the like, using a tableting mortar, and upper and lower tableting pestles. Tableting is controlled such that tablets obtained have a suitable hardness and quickly disintegrate as orodispersible tablets. A tableting pressure is adjusted as appropriate depending on the tableting method, the apparatus used for tableting, the tablet size, the principal agent, and the like. For example, when the above-described apparatus is used, the tableting pressure is normally 50 to 1,500 kg/cm$^2$, and preferably 300 to 1,000 kg/cm$^2$.

There is no particular limitation on the vehicles, and examples thereof include the substances used in the above-described granulation process. The vehicle is preferably mannitol, crystalline cellulose, lactose, or starch. These substances can be used alone or in a combination of two or more.

There is no particular limitation on the disintegrators, and examples thereof include crospovidone, crystalline cellulose, carboxymethyl cellulose (carmellose), croscarmellose sodium, carboxymethyl cellulose calcium, hydroxypropyl cellulose having a low degree of substitution, starch, partially pregelatinized starch, sodium starch glycolate, hydroxypropyl starch, calcium carbonate, precipitated calcium carbonate, calcium citrate, light anhydrous silicic acid, and synthetic aluminum silicate. The disintegrator is preferably carmellose, croscarmellose, croscarmellose sodium, carboxy starch sodium, starch, hydroxypropyl starch, or crospovidone. These substances can be used alone or in a combination of two or more. The disintegrator content is normally 0.1 to 30% by mass, preferably 0.5 to 25% by mass, and more preferably 2 to 15% by mass.

There is no particular limitation on the binders, and examples thereof include the substances used in the above-described granulation process. The binder is preferably composite particles, hydroxypropyl cellulose, or polyvinyl pyrrolidone. These substances can be used alone or in a combination of two or more.

There is no particular limitation on the corrigents, and examples thereof include aspartame, stevia, sugar alcohol, saccharin sodium, dipotassium glycyrrhizinate, thaumatin, acesulfame potassium, and sucralose. The corrigent is preferably aspartame, thaumatin, or acesulfame potassium. These substances can be used alone or in a combination of two or more.

There is no particular limitation on the lubricants, and examples thereof include stearic acid, sodium stearyl fumarate, magnesium stearate, calcium stearate, sucrose fatty acid ester, polyethylene glycol, light anhydrous silicic acid, hydrogenated oil, glycerine fatty acid ester, and talc. The lubricant is preferably sodium stearyl fumarate, magnesium stearate, calcium stearate, or sucrose fatty acid ester. These substances can be used alone or in a combination of two or more.

(Orodispersible Tablet)

When the orodispersible tablet of the present invention produced by the production method described above is subjected to sensory evaluation by people, an unpleasant taste is hardly sensed. Also, when the orodispersible tablet is checked using a taste sensor, an unpleasant taste sensed is not more than ⅕ of that of bulk drug of the principal agent.

There is no particular limitation on the form of the tablet of the present invention, and examples thereof include a disk form, a doughnut form, a polygonal plate form, a sphere form, an ellipse form, and a caplet form. There is no limitation on the size of the tablet, and the tablet has a diameter of approximately 3 to 30 mm and a thickness of approximately 1 to 10 mm, for example. The hardness of the tablet is preferably 40 to 80 N. The disintegration time of the tablet, when being taken without water, is preferably 60 seconds in the oral cavity.

EXAMPLES

Hereinafter, the present invention will be described in more detail by way of examples and comparative examples, but is not limited thereto.

Example 1

According to processes described below, orodispersible tablets (300 mg per tablet) containing diclofenac sodium (manufactured by Amoli Organics Pvt. Ltd.) as the principal agent were produced.

(Composite Particle Producing Process)

Composite particles were obtained by drying a solution obtained by dissolving and dispersing 2 parts by mass of hydrous silicon dioxide (manufactured by Fuji Silysia Chemical Ltd.) and 3 parts by mass of D-mannitol (manufactured by Roquette Japan K.K.) in 10 parts by mass of water using a spray dryer.

(Granulation Process)

Particles were obtained by putting 245 parts by mass of diclofenac sodium, 52.5 parts by mass of D-mannitol, 7 parts by mass of croscarmellose sodium (manufactured by Asahi Kasei Chemicals Corporation), and 7 parts by mass of talc (manufactured by Fuji Talc Industrial Co., Ltd.) into a mixer granulator, mixing them, and then putting a solution obtained by dissolving 24.5 parts by mass of citric acid (manufactured by Fuso Chemical Co., Ltd.) and 14 parts by mass of hydroxypropyl cellulose (SSL, manufactured by Nippon Soda Co., Ltd.) in 110 parts by mass of water into the mixer granulator. These particles were dried and subjected to particle size regulation, and principal agent particles were obtained.

(Coating Process)

Coated particles were obtained by putting 300 parts by mass of the obtained principal agent particles into a Wurster fine particle coating apparatus, and then putting a solution obtained by dissolving and dispersing 450 parts by mass of a 30% aqueous dispersion of methacrylic acid copolymer LD (EUDRAGIT L30-D55, manufactured by Evonic Degussa Co., Ltd), 13.5 parts by mass of PEG6000 (manufactured by Sanyo Chemical Industries Co., Ltd), and 31.5 parts by mass of D-mannitol in 1,005 parts by mass of water into the coating apparatus to coat the particles.

(Tableting Process)

Orodispersible tablets were obtained by mixing 19 parts by mass of the obtained coated particles, 59.9 parts by mass of D-mannitol, 10 parts by mass of crystalline cellulose (KG802, manufactured by Asahi Kasei Chemicals Corporation), 2 parts by mass of the above-described composite particles, 3 parts by mass of crospovidone (XL-10, manufactured by ISP Inc.), 3 parts by mass of carmellose (manufactured by Gotoku Chemical Co., Ltd.), 0.1 parts by mass of l-menthol (manufactured by Wako Pure Chemical Industries, Ltd.), 1.5 parts by mass of aspartame (manufactured by Ajinomoto Co., Inc.), and 1.5 parts by mass of sodium stearyl fumarate (manufactured by Riverson & Co., Ltd.), and then tableting the mixture such that the tablet is a tablet form of 9 mm double R having a mass of 300 mg.

Example 2

According to processes described below, orodispersible tablets (300 mg per tablet) containing diclofenac sodium as the principal agent were produced.

(Granulation Process)

Particles were obtained by putting 175 parts by mass of diclofenac sodium, 123 parts by mass of D-mannitol, 4 parts by mass of croscarmellose sodium, and 8 parts by mass of talc into a mixer granulator, mixing them, and then putting a solution obtained by dissolving 24 parts by mass of citric acid and 16 parts by mass of hydroxypropyl cellulose in 110 parts by mass of water into the mixer granulator. These particles were dried and subjected to particle size regulation, and principal agent particles were obtained.

(Coating Process)

Coated particles were obtained by putting 300 parts by mass of the obtained principal agent particles into a Wurster fine particle coating apparatus, putting a solution obtained by dissolving and dispersing 300 parts by mass of a 30% aqueous dispersion of methacrylic acid copolymer LD, 9 parts by mass of triacetin (manufactured by Yuki Gosei Kogyo Co., Ltd), and 21 parts by mass of D-mannitol in 850 parts by mass of water in the coating apparatus to coat the particles, and further putting a solution obtained by dissolving 45 parts by mass of D-mannitol in 300 parts by mass of water into the coating apparatus to coat the particles.

(Tableting Process)

Orodispersible tablets were obtained by mixing 25.83 parts by mass of the obtained coated particles, 53.07 parts by mass of D-mannitol, 10 parts by mass of crystalline cellulose, 2 parts by mass of the above-described composite particles, 3 parts by mass of crospovidone, 3 parts by mass of carmellose, 0.1 parts by mass of l-menthol, 1.5 parts by mass of aspartame, and 1.5 parts by mass of sodium stearyl fumarate, and then tableting the mixture such that the tablet is a tablet form of 9 mm double R having a mass of 300 mg.

Example 3

According to processes described below, orodispersible tablets (300 mg per tablet) containing losartan potassium (manufactured by Daito Pharmaceutical Co., Ltd.) as the principal agent were produced.

(Granulation and Coating Processes)

A granulated substance was obtained by putting 225 parts by mass of losartan potassium, 30 parts by mass of lactose, 7.5 parts by mass of hydroxypropyl cellulose having a low degree of substitution, and 6 parts by mass of talc into a Wurster fine particle coating apparatus, and then spraying a solution obtained by dissolving 13.5 parts by mass of hydroxypropyl cellulose and 18 parts by mass of citric acid in 168.5 parts by mass of water thereon. Then, coated particles were obtained by spraying, on the granulated substance, a solution obtained by dissolving and dispersing 400 parts by mass of a 30% aqueous dispersion of methacrylic acid copolymer LD, 12 parts by mass of triethyl citrate, and 18 parts by mass of D-mannitol in 670 parts by mass of water.

(Tableting Process)

Orodispersible tablets were obtained by mixing 100 parts by mass of the obtained coated particles, 123.5 parts by mass of D-mannitol, 45 parts by mass of crystalline cellulose, 9 parts by mass of crospovidone, 6 parts by mass of hydrous silicon dioxide, 12 parts by mass of acesulfame potassium, and 4.5 parts by mass of sodium stearyl fumarate, and then tableting the mixture such that the tablet is a tablet form of 9 mm double R having a mass of 300 mg.

Comparative Example 1

According to processes described below, orodispersible tablets (300 mg per tablet) containing diclofenac sodium as the principal agent were produced.

(Granulation Process)

Particles were obtained by putting 245 parts by mass of diclofenac sodium, 77 parts by mass of D-mannitol, 7 parts by mass of croscarmellose sodium, and 7 parts by mass of talc into a mixer granulator, mixing them, and then putting a solution obtained by dissolving 14 parts by mass of hydroxypropyl cellulose in 110 parts by mass of water into the mixer granulator. These particles were dried and subjected to particle size regulation, and principal agent particles were obtained.

(Coating Process)

Coated particles were obtained by putting 300 parts by mass of the obtained principal agent particles into a Wurster fine particle coating apparatus, and then putting a solution obtained by dissolving and dispersing 450 parts by mass of a 30% aqueous dispersion of methacrylic acid copolymer LD, 13.5 parts by mass of PEG6000, and 31.5 parts by mass of D-mannitol in 1,005 parts by mass of water into the coating apparatus to coat the particles.

(Tableting Process)

Orodispersible tablets were obtained by mixing 19 parts by mass of the obtained coated particles, 59.9 parts by mass of D-mannitol, 10 parts by mass of crystalline cellulose, 2 parts by mass of the above-described composite particles, 3 parts by mass of crospovidone, 3 parts by mass of carmellose, 0.1 parts by mass of 1-menthol, 1.5 parts by mass of aspartame, and 1.5 parts by mass of sodium stearyl fumarate, and then tableting the mixture such that the tablet is a tablet form of 9 mm double R having a mass of 300 mg.

Comparative Example 2

According to processes described below, orodispersible tablets (300 mg per tablet) containing diclofenac sodium as the principal agent were produced.

(Granulation Process)

Particles were obtained by putting 175 parts by mass of diclofenac sodium, 147 parts by mass of D-mannitol, 4 parts by mass of croscarmellose sodium, and 8 parts by mass of talc into a mixer granulator, mixing them, and then putting a solution obtained by dissolving 16 parts by mass of hydroxypropyl cellulose in 110 parts by mass of water into the mixer granulator. These particles were dried and subjected to particle size regulation, and principal agent particles were obtained.

(Coating Process)

Coated particles were obtained by putting 300 parts by mass of the obtained principal agent particles into a Wurster fine particle coating apparatus, then putting a solution obtained by dissolving and dispersing 300 parts by mass of a 30% aqueous dispersion of methacrylic acid copolymer LD, 9 parts by mass of triacetin, and 21 parts by mass of D-mannitol in 850 parts by mass of water into the coating apparatus to coat the particles, and further putting a solution obtained by dissolving 45 parts by mass of D-mannitol in 300 parts by mass of water into the coating apparatus to coat the particles.

(Tableting Process)

Orodispersible tablets were obtained by mixing 25.83 parts by mass of the obtained coated particles, 53.07 parts by mass of D-mannitol, 10 parts by mass of crystalline cellulose, 2 parts by mass of the above-described composite particles, 3 parts by mass of crospovidone, 3 parts by mass of carmellose, 0.1 parts by mass of 1-menthol, 1.5 parts by mass of aspartame, and 1.5 parts by mass of sodium stearyl fumarate, and then tableting the mixture such that the tablet is a tablet form of 9 mm double R having a mass of 300 mg.

Comparative Example 3

According to processes described below, orodispersible tablets (300 mg per a tablet) containing diclofenac sodium as the principal agent were produced.

(Granulation Process)

Particles were obtained by putting 245 parts by mass of diclofenac sodium, 52.5 parts by mass of D-mannitol, 7 parts by mass of croscarmellose sodium, and 7 parts by mass of talc into a mixer granulator, mixing them, and then putting a solution obtained by dissolving 24.5 parts by mass of citric acid and 14 parts by mass of hydroxypropyl cellulose in 110 parts by mass of water into the mixer granulator. These particles were dried and subjected to particle size regulation, and principal agent particles were obtained.

(Tableting Process)

Orodispersible tablets were obtained by mixing 11.9 parts by mass of the obtained principal agent particles, 67 parts by mass of D-mannitol, 10 parts by mass of crystalline cellulose, 2 parts by mass of the above-described composite particles, 3 parts by mass of crospovidone, 3 parts by mass of carmellose, 0.1 parts by mass of 1-menthol, 1.5 parts by mass of aspartame, and 1.5 parts by mass of sodium stearyl fumarate, and then tableting the mixture such that the tablet is a tablet form of 9 mm double R having a mass of 300 mg.

Comparative Example 4

According to processes described below, orodispersible tablets (300 mg per a tablet) containing losartan potassium as the principal agent were produced.

(Granulation and Coating Processes)

A granulated substance was obtained by putting 225 parts by mass of losartan potassium, 48 parts by mass of lactose, 7.5 parts by mass of hydroxypropyl cellulose having a low degree of substitution, and 6 parts by mass of talc into a Wurster fine particle coating apparatus, and then spraying a solution obtained by dissolving 13.5 parts by mass of hydroxypropyl cellulose in 168.5 parts by mass of water thereon. Then, coated particles were obtained by spraying a solution obtained by dissolving and dispersing 400 parts by mass of a 30% aqueous dispersion of methacrylic acid copolymer LD, 12 parts by mass of triethyl citrate, and 18 parts by mass of D-mannitol in 670 parts by mass of water on the granulated substance.

(Tableting Process)

Orodispersible tablets were obtained by mixing 100 parts by mass of the obtained coated particles, 123.5 parts by mass of D-mannitol, 45 parts by mass of crystalline cellulose, 9 parts by mass of crospovidone, 6 parts by mass of hydrous silicon dioxide, 12 parts by mass of acesulfame potassium, and 4.5 parts by mass of sodium stearyl fumarate, and then tableting the mixture such that the tablet is a tablet form of 9 mm double R having a mass of 300 mg.

(Evaluation of the Obtained Tablets)

As shown below, masking of a bitter taste, disintegration time, and eluting behavior of the tablets of Examples and the tablets of Comparative Examples were evaluated.

(Evaluation of Masking of Bitter Taste)

The tablets of Examples and the tablets of Comparative Examples were taken by three test subjects, and the bitter taste of each tablet was evaluated. The evaluation results of the orodispersible tablets containing diclofenac sodium as the principal agent are shown in Table 1, and the evaluation results of the orodispersible tablets containing losartan potassium as the principal agent are shown in Table 2.

TABLE 1

| | Test Subject A | Test Subject B | Test Subject C |
|---|---|---|---|
| Example 1 | 1 | 2 | 2 |
| Example 2 | 1 | 1 | 1 |
| Comparative Example 1 | 3 | 4 | 3 |
| Comparative Example 2 | 3 | 3 | 3 |
| Comparative Example 3 | 4 | 4 | 3 |

1: Almost no bitterness;
2: Little bitterness,
3: Strong bitterness;
4: Very strong bitterness As is clear from Table 1, the tablets of Comparative Examples 1 and 2 in which citric acid was not used in the granulation process, and the tablets of Comparative Example 3 in which the coating process was not performed had strong bitterness when they were taken, because the bitter taste was insufficiently masked. On the other hand, the tablets of Examples 1 and 2 in which citric acid was used in the granulation process, and a pH-dependent polymer was used in the coating process had almost no or a little bitterness when they were taken, because the bitter taste was sufficiently masked.

TABLE 2

|  | Test Subject A | Test Subject B | Test Subject C |
|---|---|---|---|
| Example 3 | 1 | 2 | 2 |
| Comparative Example 4 | 3 | 4 | 4 |

1: Almost no bitterness;
2: Little bitterness,
3: Strong bitterness;
4: Very strong bitterness As is clear from Table 2, the tablets of Comparative Example 4 in which citric acid was not used in the granulation and coating processes had strong bitterness when they were taken, because the bitter taste was insufficiently masked. On the other hand, the tablets of Example 3 in which citric acid was used in the granulation and coating processes had almost no or a little bitterness when they were taken, because the bitter taste was sufficiently masked.

(Evaluation of Disintegration Time)

The tablets of Examples 1 and 2, and the tablets of Comparative Examples 1 to 3 were taken by three test subjects, and a disintegration time of each tablet was evaluated. The results were shown in Table 3.

TABLE 3

|  | Disintegration time (sec.) | | |
|---|---|---|---|
|  | Test Subject A | Test Subject B | Test Subject C |
| Example 1 | 35 | 39 | 40 |
| Example 2 | 20 | 32 | 30 |
| Comparative Example 1 | 30 | 35 | 29 |
| Comparative Example 2 | 18 | 27 | 27 |
| Comparative Example 3 | 17 | 22 | 27 |

The disintegration time of each of the tablets of Examples 1 and 2, and the tablets of Comparative Examples 1 to 3 was measured using a Tricorptester under the conditions of a dropping rate of 6.0 g/minute, a dropping height of 8 cm, and a load of 40 g. The results were shown in Table 4. Table 4 shows the results when n=6.

TABLE 4

|  | Disintegration Time (sec.) | |
|---|---|---|
|  | Average | Standard Deviation |
| Example 1 | 18.45 | 0.79 |
| Example 2 | 15.00 | 0.65 |
| Comparative Example 1 | 21.42 | 1.69 |
| Comparative Example 2 | 14.45 | 1.18 |

TABLE 4-continued

|  | Disintegration Time (sec.) | |
|---|---|---|
|  | Average | Standard Deviation |
| Comparative Example 3 | 18.65 | 1.76 | n = 6

As is clear from Tables 3 and 4, the tablets of Examples 1 and 2 showed similar disintegrating behavior to the tablets of Comparative Examples 1 to 3.

(Evaluation of Eluting Behavior)

Soon after being tableted, an eluting ratio of each of the tablets of Example 2 and Comparative Example 2 was measured using the second solution of the Japanese Pharmacopoeia elution method in the test by the paddle method (37° C., 50 rpm). The results were shown in Table 5. Table 5 shows the results when n=3.

TABLE 5

|  | Elution Rate (%) | | | |
|---|---|---|---|---|
|  | Example 2 | | Comparative Example 2 | |
| Elapsed Time from the Start of Test (min.) | Average | Standard Deviation | Average | Standard Deviation |
| 5 | 89.5 | 2.5 | 92.7 | 6.2 |
| 10 | 100.5 | 2.1 | 100.1 | 0.4 |
| 15 | 101.6 | 1.8 | 100.7 | 1.2 |
| 30 | 101.9 | 2.0 | 100.7 | 0.8 | n = 3

As is clear from Table 5, although citric acid was used in the granulation process, the tablets of Examples 1 and 2 showed similar elution behavior to the tablets of Comparative Examples 1 to 3.

INDUSTRIAL APPLICABILITY

The present invention can provide a method for easily producing orodispersible tablets that secure elution of a principal agent in the digestive tract and mask an unpleasant taste in the oral cavity.

The invention claimed is:

1. A method for producing orodispersible tablets comprising:
   mixing an additive to a principal agent to form principal agent particles as a granulation process;
   coating the principal agent particles with a coating agent to form coated particles as a coating process; and
   forming the coated particles to form tablets as a tableting process,
   wherein the principal agent is an acidic substance having a drug effect, the additive used in the granulation process comprises a pH regulator, which is used in a solution obtained by dissolving the pH regulator, the coating agent used in the coating process comprises a pH-dependent polymer dissolving at pH 5 or more, and
   wherein the pH regulator comprises at least one acidic substance selected from a group consisting of adipic acid, citric acid, malic acid, fumaric acid, succinic acid, tartaric acid, aspartic acid, and glutamic acid, and salts thereto.

2. The method of claim 1, wherein a concentration of the pH regulator per 1 g of the principal agent is between 10 and 1,000 mg.

3. The method of claim 1, wherein a concentration of the pH-dependent polymer per 1 g of the principal agent is between 50 and 2,000 mg.

4. The method of claim 2, wherein a concentration of the pH-dependent polymer per 1 g of the principal agent is between 50 and 2,000 mg.

* * * * *